United States Patent [19]

Blackwell et al.

[11] Patent Number: 4,478,864

[45] Date of Patent: Oct. 23, 1984

[54] CONFECTIONS CONTAINING STABILIZED PEPPERMINT OIL

[75] Inventors: Bernie Blackwell, Laurelton, N.Y.; Shelley Netherwood, Brea, Calif.; Dominick J. Piccolo, Brooklyn, N.Y.

[73] Assignee: Warner-Lambert Company, Morris Plains, N.J.

[21] Appl. No.: 570,472

[22] Filed: Jan. 23, 1984

Related U.S. Application Data

[62] Division of Ser. No. 450,870, Dec. 20, 1982, Pat. No. 4,440,790.

[51] Int. Cl.$^3$ .................... A23G 3/00; A23L 1/222
[52] U.S. Cl. .................... 426/534; 426/651; 426/660
[58] Field of Search ............... 426/533, 534, 660, 651

[56] References Cited

U.S. PATENT DOCUMENTS 2,435,744  2/1948  Hartman .................. 426/651
3,083,105  3/1963  Todd ...................... 260/236.6
4,259,355  3/1981  Marmo .................... 426/651

FOREIGN PATENT DOCUMENTS 33250  5/1973  Japan .................... 426/651

OTHER PUBLICATIONS

Arctander, Perfume and Flavor Chemicals II, pub. Arctander, 1969, Montclair, N.J. 91 1838.

*Primary Examiner*—Jeanette M. Hunter
*Attorney, Agent, or Firm*—Gary M. Nath; Daniel A. Scola, Jr.

[57] ABSTRACT

Peppermint oil containing a reduced methofuran content is prepared by reacting the peppermint oil with about 0.5% to about 15% by weight maleic anhydride, based on the weight of peppermint oil to selectively form a menthofuran-maleic anhydride adduct without otherwise affecting the flavoring agent properties of the remaining peppermint oil constituents and recovering the peppermint oil therefrom.

15 Claims, 2 Drawing Figures

CONFECTIONS CONTAINING STABILIZED PEPPERMINT OIL

This is a divisional application of Ser. No. 06/450,870, filed Dec. 20, 1982, now U.S. Pat. No. 4,440,790.

This invention relates to a method for stabilizing peppermint oil, and more particularly to preparing a peppermint oil having a reduced menthofuran content.

Peppermint oil is a well know favoring agent derived from the leaves and flowering tops of the plant (*Mentha poperita L*). The plants habitate is quite diverse and has been found in parts of Asia, Europe, and North America.

The peppermint oil constituents will vary depending on the source of the plant even though several main constituents are usually present. In general, peppermint oil contains varying amounts of alpha-pinene, beta-pinene, limonene, 1,8-cineole, menthone, menthofuran, isomenthol, menthyl acetate, neomenthol and menthol as well as various amounts of other constituents.

A disadvantage associated with the use of peppermint oil in the past has been its degradation during storage resulting in change in odor and flavor properties. Several studies have undertaken to identify the aging characteristics of peppermint oil.

One study is described by R. H. Reitsema, et al. in *Oxidation of Peppermint Oil,* Industrial and Engineering Chemistry, Vol 44, page 176, January 1952, wherein three reactions are described as contributing to the aging process. The first reaction is the isomerization of terpenes which is described as having only minor importance. The second reaction involves the polymerization of the oil constituents which is noted as increasing the oils molecular weight and the viscosity of the resulting product. And thirdly, the most important reaction is identified as the oxidation of the peppermint oil which affects aging of the oil from a flavor standpoint. Specific components involved in the oxidation aging process include the pinenes, limonene and menthofuran.

Various attempts have been made to inhibit the oxidation process to prevent the formation of oxidative by-products commonly referred to as "off-note" material. One conventional technique involves the use of antioxidants in the peppermint oil in an effort to inhibit the reaction from occurring. The use of such antioxidants, however, have not been successful since they are either not effective in suppressing the oxidation reaction over prolonged storage conditions or they have resulted in the formation of "off-note" peppermint oil detracting from the flavoring agent properties. These processes at best have merely attempted to mask the oxidation process by-products without removing the oxidative constituents from the oil themselves.

Another attempt to overcome the oxidation phenomenon is disclosed by Guenter in *The Essential Oils,* Vol III (1949), page 619. This reference discloses use of a fractional distillation technique to separate the peppermint oil flavor constituents from menthofuran. This technique was unsuccessful, however, since the menthofuran was codistilled with menthone, a major flavoring component of peppermint oil, rendering the recovered product unsuitable for use as a flavoring agent.

A procedure has been unexpectedly discovered which selectively removes one of the primary "off-note" oxidative by-product contributors, namely menthofuran. In particular, a procedure has been unexpectedly discovered which successfully accomplishes the selective removal of a portion of the menthofuran from peppermint oil in order to produce a storage stable peppermint oil flavoring agent. The reduced menthofuran peppermint oil product of this invention unexpectedly demonstrates resistance to the formation of oxidative "off-note" material and thus renders this product extremely useful in a wide variety of products.

In accordance with the present invention there is provided a process for preparing a peppermint oil containing a reduced menthofuran content, which comprises reacting the peppermint oil with about 0.5% to about 15% by weight maleic anhydride, based on the weight of peppermint oil to selectively form a menthofuran-maleic anhydride adduct without otherwise affecting the flavoring agent properties of the remaining peppermint oil constituents and recovering a peppermint oil having a reduced menthofuran content.

Another aspect of the invention involves preparing a stabilized peppermint oil which comprises (a) admixing peppermint oil with from about 0.5% to about 15% by weight maleic anhydride, based on the weight of peppermint oil; (b) maintaining the admixture at a temperature of from about 0° C. to about 80° C. to prepare a reaction admixture containing a menthofuran-maleic anhydride adduct within the peppermint oil; (c) separating the menthofuranmaleic anhydride adduct from the peppermint oil; and (d) recovering the peppermint oil which contains a reduced menthofuran content.

Figure 1:
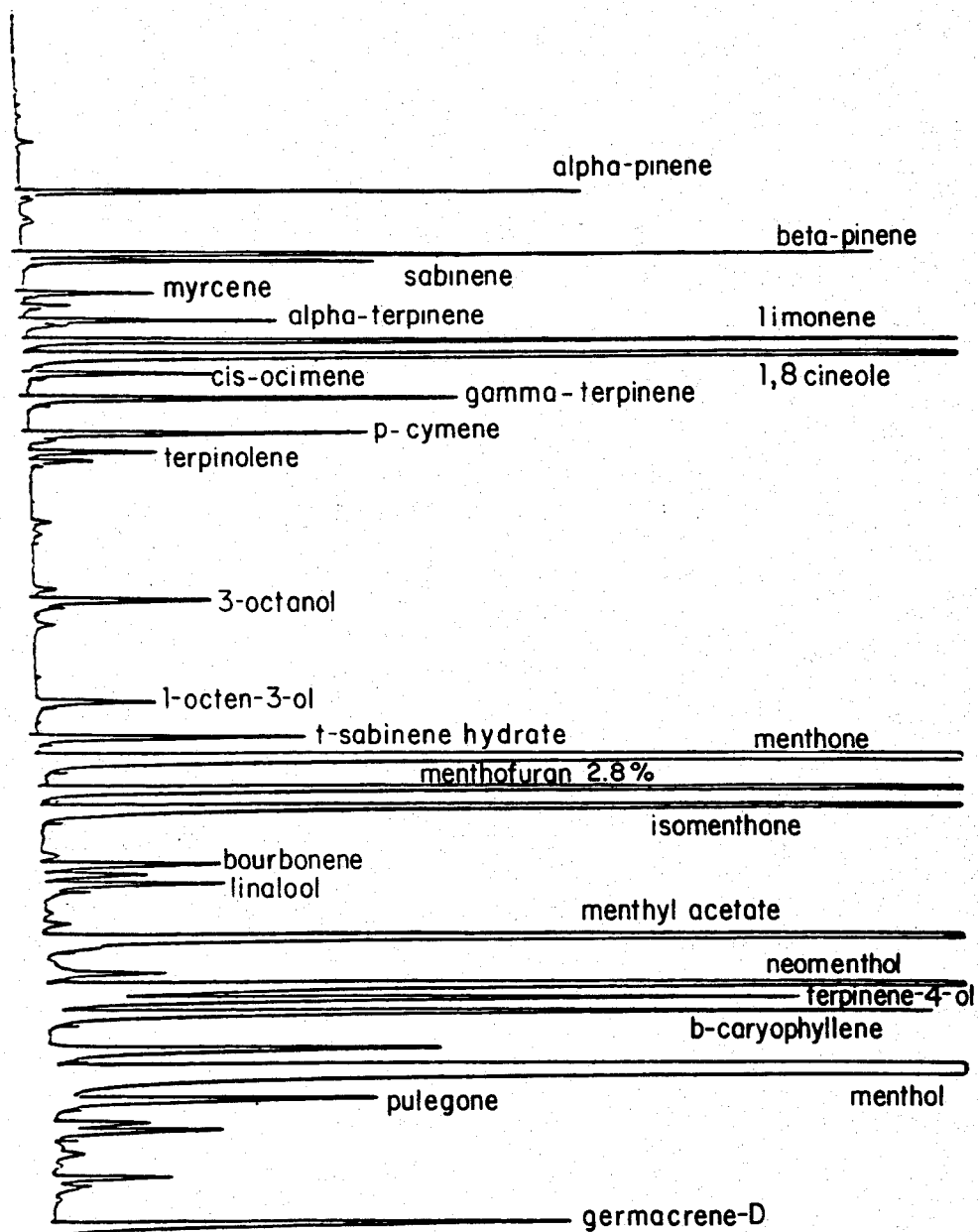
FIG. 1 represents a gas chromatography analysis of a peppermint oil.
Figure 2:
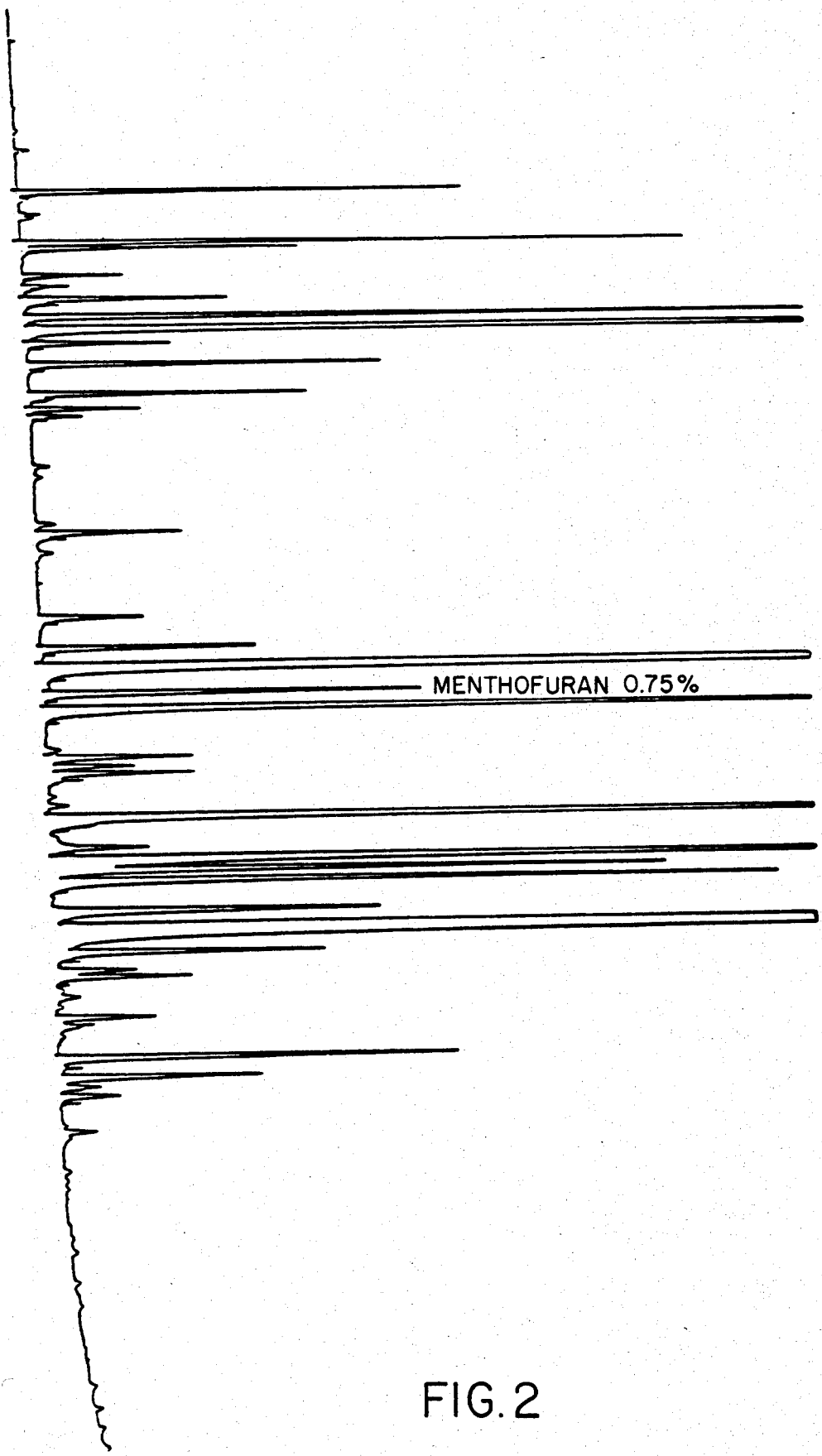
FIG. 2 represents a gas chromatography analysis of a peppermint oil treated according to the invention, both more fully described in Example II.

According to the process of the present invention, maleic anhydride is added to peppermint oil in a particular manner to selectively form an adduct product comprising a complex of menthofuran and maleic anhydride. This adduct is then separated from the peppermint oil to prepare a stabilized peppermint oil containing a reduced menthofuran content.

The structure of menthofuran is chemically known as tetrahydro-4,5,6,7-dimethyl-3,5-coumarone and is routinely found in peppermint oil in amounts up to 15% and generally in amounts from 1 to 10% based on the weight of the peppermint oil.

The addition of maleic anhydride to peppermint oil to identify the existence and presence of menthofuran was proposed by P. Bedoukian, *Journal of American Chemical Society,* Vol 70, page 621, 1948 and R. Eastman, *Journal of American Chemical Society,* Vol 72, page 5313, 1950. Both Bedoukian and Eastman disclose the formation of a crystalline material, theorized to be menthofuran-maleic anhydride adduct, upon the addition of maleic anhydride to peppermint oil in the presence of a benzene solvent. The impure peppermint oil containing benzene was discarded and the menthofuran chemically identified. Each of these techniques employed excess maleic ahhydride and benzene as a solvent to stabilize the menthofuran-maleic anhydride adduct.

In contrast to these prior art techniques, applicants have used this basic reaction in an unexpected manner to purify peppermint oil.

Applicants have unexpectedly found that this reaction can be used to prepare a low menthofuran peppermint oil which has superior resistance to the formation of oxidative "off-note" material or musty odor associated with the oxidation by-products.

It has been found that if a sufficient amount of maleic anhydride is added to the peppermint oil a menthofuran-maleic anhydride adduct is formed which does not concurrently enable formation of secondary by-products rendering the oil unusable. A proposed scheme for the adducts formation is illustrated as follows:

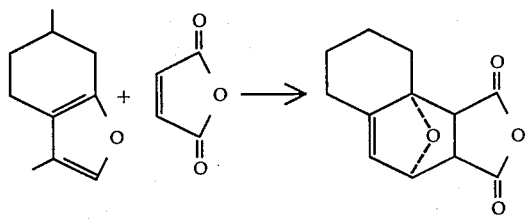

It appears from the stiochiometry of the reaction that the adduct may result from a Diels-Alder type addition and that the 1,4 conjugated diene system in the menthofuran attaches to the carbon-carbon double bond between the two carbonyl groups in maleic anhydride. Once the adduct is removed from the peppermint oil, the resulting oil has the normal constituent profile and balance of the starting oil but with a reduced menthofuran content.

The amount of maleic anhydride employed in this process must be sufficient to complex with a portion of the menthofuran to enable a portion to be retented in low amounts in the peppermint oil. Acceptable amounts have been found to be the stoichiometric amount and less than the stoichiometric amount of maleic anhydride to the menthofuran content. When excess amounts of maleic anhydride are employed remove of all of the menthofuran from the peppermint oil is achieved. The resulting peppermint oil product, however, has a modified appearance and noticeable "off-note" flavor and package aroma. Accordingly, the process of the invention is performed in a manner to remove only a portion of the menthofuran while enhancing the stability of the peppermint oil.

Generally, the low menthofuran peppermint oil of this invention has a menthofuran content after treatment below about 2.0%, and preferably between about 0.8 and about 1.4%, and most preferably between about 0.8% and about 1%, all based on the weight of peppermint oil. This amount of menthofuran is achieved by using from about 0.5% to about 15% by weight maleic anhydride by weight of peppermint oil. It should be recognized that the exact amount of maleic anhydride employed will vary depending upon the menthofuran content of the oil and the degree of reduction desired.

It has been found that use of stoichiometric amounts of maleic anhydride to the menthofuran content results in lowering the menthofuran content to acceptable levels without completely complexing all the maleic anhydrite to form the maleic anhydride-menthofuran adduct. This is achieved by the formation of free maleic acid in the peppermint oil resulting from the hydrolysis reaction of maleic anhydride and water, water being inherently present in the peppermint oil.

In a preferred embodiment of the invention the peppermint oil containing menthofuran is admixed with the maleic anhydride and stirred to solubilize the maleic anhydride. The reaction between the menthofuran and the maleic anhydride commences almost instantaneously resulting in an exothermic reaction.

The temperature of the reaction admixture is preferably maintained between about 0° C. and about 80° C. and most preferably between about 25° C. and about 50° C. Temperatures below 0° C. tend to result in the gelation of the oil while temperatures above 80° C. may cause accelerated oxidation and polymerization of the oil constituents. It should be recognized that the reaction is exothermic in nature and use of standard means to maintain the reaction temperature are contemplated to be used and within the skill of the ordinary artisan.

The reaction time is not critical and will vary depending upon the particular reaction temperature employed, faster reaction times occur at higher temperatures, and longer reaction times occur at lower temperatures. For commercial reasons the reaction time may vary from a few seconds up to 12 hours and preferable up to about 5 hours even though longer times (for example up to 4 weeks) at lower temperatures are useable.

Once the reaction is complete the menthofuran-maleic anhydride adduct is separated from the low menthofuran peppermint oil; that is the purified peppermint oil. Since the menthofuran-maleic anhydride adduct is crystalline in peppermint oil at temperatures below 5° C. separation is conveniently performed by lowering the temperature of the admixture to crystallize the menthofuran-maleic anhydride adduct. The resulting peppermint oil is then recovered by conventional solid-liquid separation means such as filtration or decantation.

In a preferred embodiment, the reaction admixture containing peppermint oil and the menthofuran-maleic anhydride adduct is contacted with an aqueous basic solution prior to crystallization. This optional embodiment enables the neutralization of any free maleic acid present in the peppermint oil. The presence of free maleic acid may alter the flavor and aroma properties of the purified oil if not removed.

The neutralization reaction is performed with any basic composition that will react with the maleic acid to form its corresponding water soluble salt. Suitable exemplary inorganic base materials include sodium carbonate and bicarbonate, potassium carbonate, calcium carbonate, sodium sulfate, potassium sulfate, calcium sulfate, sodium phosphate, potassium phosphate, calcium phosphate, sodium formate, potassium formate, calcium formate, sodium nitrate, potassium nitrate, calcium nitrate and mixtures thereof. The preferred base is sodium carbonate, but in short any inorganic material may be used which forms the maleate salt and which does not adversely affect the peppermint oil composition to which it is admixed.

The amount of aqueous basic solution added to the peppermint oil reaction admixture may be any amount which results in the neutralization of the free maleic acid. Typically, use of about 0.5% to about 20%, and most preferably about 10% by weight basic solution is sufficient, based on the weight of the peppermint oil.

The neutralization reaction is performed in a conventional manner by simply mixing the aqueous basic solution with the peppermint oil reaction mixture. Once mixed the resulting oil-water emulsion is permitted to separate into their respective phases, that is an oil phase containing the peppermint oil and the menthofuran-maleic anhydride adduct, and a water phase containing free unreacted base, the maleate salt and any water soluble impurities associated with the oil. The oilwater phases are then separated by conventional liquid liquid separation techniques such as decantation with the aqueous phase discarded and the oil phase processed to remove the menthofuran-maleic anhydride as by crystallization technique described above.

Alternatively, if desired, the peppermint oil reaction admixture containing the menthofuran-maleic anhydride adduct is separated with or without prior cooling by conventional distillation techniques. The distillation operation must be performed in a manner to prevent oxidation and polymerization of the peppermint oil while enabling separation of the peppermint oil from the adduct.

Suitable exemplary distillation methods include vacuum distillation and steam distillation methods. Use of standard boiling distillation techniques are not acceptable and result in degradation of the peppermint oil. The use of vacuum distillation or steam distillation methods enables the selective removal of the unreacted peppermint oil fractions based on their respective boiling points. As in conventional steam and vacuum distillations, separation is achieved by the condensation of the vapor removed from the distillation device with its subsequent condensation.

The temperature employed during the distillation will vary widely depending upon the vacuum pressure employed to fractionally separate the peppermint oil fractions from the adduct, which temperatures represent the boiling point of the constituents at the particular pressure employed.

As in conventional vacuum distillation technique a gas may be employed during the reaction to purge the contents of particular fractions to enhance reaction speed and efficiency. Illustrative gases include any gas that is non reactive with the peppermint oil constituents and include inert gases, such as argon and helium as well as nitrogen, carbon dioxide, and other suitable gases and mixtures thereof.

Because the boiling point of the menthofuran-maleic anhydride adduct is closely related to the higher molecular weight constituents of the peppermint oil, distillation is preferably performed until most, but not all of the peppermint oil has been removed. In this regard, it is advantageous to withdraw the peppermint oil fractions until a residue remains in the distillation flask which residue contains the adduct and a minor amount of residual unremoved peppermint oil. The residue in the distillation flask is conveniently discarded. The peppermint oil fractions, which contain a low level of unreacted menthofuran, are then recovered and combined to form the stabilized peppermint oil of this invention.

The peppermint oil containing the reduced menthofuran content may be stored or used directly as a flavoring agent by blending with foods, chewing gum, confectionary, pharmaceuticals, beverages, tobacco and proprietary products such as toothpaste and mouthwash by conventional means in amounts sufficient to provide the desired flavoring power. Acceptable amounts will vary from about 0.01% to about 5.0% by weight flavoring agent based on the weight of the final product.

The following examples are given to illustrate the invention, but are not deemed to be limiting thereof. All percentages given throughout the specification are based upon weight unless otherwise indicated.

EXAMPLE I

This example demonstrates the selective removal of menthofuran from peppermint oil.

Five hundred (500) grams of Midwest peppermint oil (A. M. Todd Company, Kalamazoo, Mich.) containing 2.8% menthofuran was mixed with 10% by weight (50 gm.) maleic anhydride in a flask. The mixture was mechanically stirred for a total of 30 minutes at 28° C. during which time a rise in temperature to 50° C. was noted. The solution was then neutralized by washing with 100 grams of 10% $Na_2CO_3$ solution. The lower hydrous layer was separated and discarded which contained $Na_2CO_3$, sodium maleate, water soluble impurities from the peppermint oil.

The peppermint oil was recovered by distillation under vacuum using a nitrogen purging atmosphere. The distillation unit consisted of a boiling flask, two fractionation columns packed with Berl Saddles, two cold water condensors, a nitrogen embulator, and a graduated vacuum collector. The distillation temperature was maintained between 24° and 86° C. in the pot with a vapor temperature around 57° C.

A product was recovered which contained reduced menthofuran peppermint oil having a yield of 461.0 gms. The menthofuran content in the recovered peppermint oil was 0.80% determined by capillary Gas Chromatography. A residue of 16.10 grams (3.00%) remained in the distillation flask which contained some peppermint oil residue, and the menthofuran-maleic anhydride adduct.

EXAMPLE II

This example compares the selective reaction of maleic anhydride with menthofuran when present in peppermint oil.

A gas chromatographic analysis of peppermint oil, both prior and subsequent to treatment with maleic anhydride, was used. The results are set forth in FIGS. I and II.

FIG. 1 depicts the gas chromatographic analysis of an American Midwest peppermint oil prior to the purification treatment of this invention.

FIG. II depicts the gas chromatographic analysis of the same peppermint oil shown in FIG. I after the purification procedure of Example I.

The analysis was performed by conventional gas-liquid chromatography techniques using a 275° injection temperature to maintain all of the sample components in the vapor state using a Hewett Packard Model 5840-A device. The column used a 30 meter glass column containing Carbowax 20M glycols (product of Union Carbide Corporation).

The Figures graphically shown the individual components of peppermint oil as removed from the column. The results indicate that maleic anhydride selectively reacts with menthofuran without affecting the remaining components of the peppermint oil. This selective reaction enables a reduction in the methofuran content to be easily achieved without affecting the flavoring agent properties of the peppermint oil associated with the remaining constituents.

The invention being thus described, it will be obvious that the same may be varied in many ways. Such variations are not to be regarded as a departure from the spirit and scope of the invention and all such modifications are intended to be included within the scope of the following claims.

What we claim is:

1. A method of flavoring, confectionary, which comprises adding thereto an effective amount of stabilized peppermint oil flavoring agent prepared by reacting the peppermint oil with about 0.5% to about 15% by weight maleic anhydride, based on the weight of peppermint oil to selectively form a menthofuran-maleic anhydride adduct without otherwise affecting the flavoring agent properties of the remaining peppermint oil constituents and recovering the peppermint oil having a reduced menthofuran content.

2. The process of claim 1 wherein the menthofuran content in the recovered peppermint oil is from about 0.8 to about 1.4% based on the weight of peppermint oil.

3. The process of claim 1 wherein the amount of maleic anhydride is the stiochiometric amount needed to react with the menthofuran present in the peppermint oil.

4. The process of claim 1 wherein the amount of maleic anhydride is less than the stiochiometric amount needed to react with the menthofuran present in the peppermint oil.

5. The process of claim 1 wherein the peppermint oil is recovered by vacuum distillation or steam distillation from the reaction mixture containing peppermint oil and a menthofuran-maleic anhydride adduct.

6. A method of flavoring confectionery, which comprises adding thereto an effective amount of stabilized peppermint oil flavoring agent prepared by
   (a) admixing peppermint oil with from about 0.5% to about 15% by weight maleic anhydride, based on the weight of peppermint oil;
   (b) maintaining the admixture at a temperature of from about 0° C. to about 80° C. to prepare a reaction admixture containing a menthofuran-maleic anhydride adduct within the peppermint oil;
   (c) separating the menthofuran-maleic anhydride adduct within the peppermint oil; and
   (d) recovering the peppermint oil which contains a reduced menthofuran content.

7. The process of claim 6 wherein the admixture is maintained at a temperature of from about 25° C. to about 50° C.

8. The process of claim 6 wherein the peppermint oil reaction admixture of step (b) is contacted with an aqueous basic solution to neutralize any free maleic acid present in the peppermint oil.

9. The process of claim 6 wherein the peppermint oil reaction admixture of step (b) is mixed with an aqueous basic solution to form two phases, an oil phase containing the peppermint oil and menthofuran-maleic anhydride adduct and an aqueous phase containing free base, a maleate salt and water soluble impurities.

10. The process of claim 9 wherein the aqueous and oil phases are separated.

11. The process of claim 6 wherein the peppermint oil reaction admixture containing the menthofuran-maleic anhydride adduct is separated by cooling the reaction admixture below its reaction temperature to crystallize the menthofuran-maleic anhydride adduct.

12. A method of flavoring confectionary which comprises adding thereto an effective amount of a stablized peppermint oil flavoring agent prepared by
   (a) admixing peppermint oil with from about 0.5% to about 15% by weight maleic anhydride, based on the weight of peppermint oil;
   (b) maintaining the admixture at a temperature of from about 0° C. to about 80° C. to prepare a reaction admixture containing peppermint oil and a menthofuran-maleic anhydride adduct;
   (c) admixing the reaction admixture containing peppermint oil and a menthofuran-maleic anhydride adduct with an aqueous basic solution to form a solution having two phases, an oil phase and a water phase;
   (d) separating the oil phase from the water phase, said oil phase containing peppermint oil and the menthofuran-maleic anhydride adduct; and
   (e) recovering the peppermint oil containing a reduced menthofuran content.

13. The process of claim 12 wherein the admixture is maintained at a temperature of from about 25° C. to about 50° C.

14. The process of claim 12 wherein the aqueous basic solution is added in a sufficient amount to neutralize any maleic acid present in the peppermint oil resulting from the hydrolysis of maleic anhydride.

15. The process of claim 12 wherein the peppermint oil is recovered by cooling the oil phase to a temperature below the reaction temperature to crystallize the menthofuran-maleic anhydride adduct, and the crystallized adduct is separated from the peppermint oil having a reduced menthofuran content.

* * * * *